United States Patent
Duffy

[11] Patent Number: 6,050,973
[45] Date of Patent: Apr. 18, 2000

[54] PRESSURE LIMITING DEVICE

[75] Inventor: Niall F. Duffy, Tuam, Ireland

[73] Assignee: AVE Connaught, Dublin, Ireland

[21] Appl. No.: 09/152,967

[22] Filed: Sep. 14, 1998

[51] Int. Cl.⁷ .................................................. A61M 29/00
[52] U.S. Cl. .............................. 604/99; 604/96; 604/247; 137/505.13
[58] Field of Search ........................ 604/97–99, 920–921, 604/246–247; 137/505.13; 606/192, 194

[56] References Cited

U.S. PATENT DOCUMENTS

| | | |
|---|---|---|
| 2,245,271 | 6/1941 | Guill . |
| 3,087,492 | 4/1963 | Garth . |
| 3,152,592 | 10/1964 | Foley . |
| 3,352,531 | 11/1967 | Kilmarx . |
| 4,062,360 | 12/1977 | Bentley . |
| 4,143,853 | 3/1979 | Abramson . |
| 4,449,693 | 5/1984 | Gereg . |
| 4,703,759 | 11/1987 | Merrick et al. . |
| 4,931,050 | 6/1990 | Idriss . |
| 5,061,253 | 10/1991 | Yoshida . |
| 5,084,021 | 1/1992 | Baldwin . |
| 5,098,405 | 3/1992 | Peterson et al. . |
| 5,221,268 | 6/1993 | Barton et al. . |
| 5,238,026 | 8/1993 | Goto . |
| 5,273,542 | 12/1993 | Blake, III . |
| 5,300,034 | 4/1994 | Behnke et al. . |
| 5,318,515 | 6/1994 | Wilk . |
| 5,336,174 | 8/1994 | Daoud et al. . |
| 5,336,192 | 8/1994 | Palestrant . |
| 5,378,229 | 1/1995 | Layer et al. .............................. 604/31 |
| 5,409,477 | 4/1995 | Caron et al. . |
| 5,453,096 | 9/1995 | Lataix . |
| 5,453,097 | 9/1995 | Paradis . |
| 5,499,968 | 3/1996 | Milijasevic et al. . |
| 5,514,110 | 5/1996 | Teh . |
| 5,520,661 | 5/1996 | Lal et al. . |
| 5,520,665 | 5/1996 | Fleetwood . |
| 5,531,688 | 7/1996 | Hiejima et al. . |
| 5,613,980 | 3/1997 | Chauhan .................................. 606/194 |
| 5,669,879 | 9/1997 | Duer .......................................... 604/96 |
| 5,669,881 | 9/1997 | Dunshoe ................................. 604/164 |

FOREIGN PATENT DOCUMENTS 0399 119  11/1990  European Pat. Off. .

Primary Examiner—Wynn Wood Coggins
Assistant Examiner—LoAn H. Thanh
Attorney, Agent, or Firm—Sterne, Kessler, Goldstein & Fox P.L.L.C.

[57] ABSTRACT

An apparatus for limiting the pressure of inflation fluid injected into one or more balloon of a catheter device comprising a reservoir chamber having an inlet port coupled in fluid communication with an inflation/deflation device and a plurality of outlet ports coupled in fluid communication with a plurality of cylindrical housings. Each cylindrical housing includes a pressure chamber and a valve chamber. The valve chamber receives a piston moveable between a fully open position and a closed position and spring biased toward the fully open position. Each housing includes an outlet port coupled in fluid communication with a separate balloon of a catheter device. Each piston includes an internal flow path which enables the flow of pressurized inflation fluid from the reservoir chamber to the balloon catheter when the pressure of the inflation fluid within the balloon is below the desired cut-off pressure. As the pressure of the inflation fluid within each balloon increases, the associated piston is urged toward its closed position. When the inflation fluid within the each balloon reaches the predetermined cut-off pressure level, the associated piston moves to the closed position and cuts-off the flow of inflation fluid from the reservoir chamber to the respective balloon.

21 Claims, 9 Drawing Sheets

PRESSURE LIMITING DEVICE

FIELD OF INVENTION

The present invention relates to a valve apparatus for limiting the pressure of inflation fluid injected into one or more balloons of a catheter device.

BACKGROUND AND OBJECTS OF THE INVENTION

Various balloon catheter designs have been developed for use in a wide range of medical catheterization procedures. Such catheterization procedures include angioplasty dilatation, stent delivery, and localized drug delivery.

Balloon catheters for angioplasty dilatation generally comprise an elongated catheter tube having proximal and distal ends, and an expandable balloon located at the distal end of the catheter tube. The catheter tube includes one or more lumens extending longitudinally throughout essentially the entire length of the tube. In its basic form, at least one of the lumens functions as a conduit for the flow of inflation fluid from the proximal end of the catheter tube to the interior of the balloon. When it is desired to inflate the balloon, pressurized inflation fluid is injected into the proximal end of the inflation lumen via a syringe or other pressure infusion device.

Balloon dilatation catheters are frequently used to dilate blood vessels restricted by an atherosclerotic lesion or stenosis. To this end, a balloon dilatation catheter is introduced into a patient's vascular system such that the dilatation balloon is positioned across the area of a narrowing. Inflation fluid is then injected through the catheter tube lumen and into the balloon. The balloon expands to press against and open the narrowed portion of the blood vessel.

The success of such a dilatation procedure largely depends on the proper inflation of the balloon, thus requiring great skill on the part of the administering physician. Should the physician provide too little pressure in injecting the inflation fluid into the catheter, the balloon will not inflate to the extent necessary and the dilatation will be insufficient. However, should the physician inject the inflation fluid into the catheter at too great of a pressure, the balloon will over-inflate thereby creating the danger of trauma to the blood vessel wall. Moreover, should the inflation fluid be injected at an excessively high pressure level, the balloon may burst.

As identified above, another balloon catheter procedure involves the delivery of a stent within a patient's vasculature. Stent delivery procedures are commonly employed in conjunction with angioplasty dilatation procedures, such as the one described above for treatment of a stenosis. It has been found that a stenosis is susceptible to collapse or restenosis following an angioplasty dilatation procedure. Thus, such angioplasty dilatation procedures are frequently followed by the implantation of a stent to prevent collapse of the stenosis or restenosis. During such a stent delivery procedure, the stenosis is opened as described above with a dilatation balloon catheter. Next, a stent, having a reduced outer diameter and carried about an expansion balloon, is positioned within the opened stenosis. Then, the expansion balloon is inflated with pressurized fluid to expand the outer diameter of the stent into engagement with the stenosis. It will be understood that because an expansion balloon is inflated with pressurized fluid to implant the stent at the stenosis, the same problems described above with regard to the proper inflation of a dilatation balloon also apply to the inflation of an expansion balloon for a stent delivery catheter. Namely, if the balloon is under-inflated, the stent may not be properly implanted. Conversely, if the balloon is over-inflated, the stent may cause trauma to the vessel walls or the balloon may burst.

Further, recent balloon catheter designs have been developed for treatment of a stenosis using a single catheter device enabling both balloon dilatation and stent delivery. To this end, such balloon catheters generally comprise a catheter tube having at least two balloons located proximate its distal end. According to this design, one of the balloons functions as a dilatation balloon and another functions as an expansion balloon which carries a crimped stent. Thus, the combined dilatation/stent delivery procedure is performed by the administering physician through the use of only one catheter device, and not separate angioplasty dilatation and stent delivery catheters. However, the above-identified problems with regard to the difficulties in properly inflating the dilatation and stent expansion balloons remain. Indeed, these problems are compounded to the extent that there are two or more balloons which must be inflated. Further complicating the balloon inflation procedure is that different inflation pressures may be required for each of the balloons.

Moreover, other stent delivery balloon catheter designs have been developed for delivering and implanting bifurcated or Y-shaped stents to a bifurcated vessel within a patient's vasculature. Generally, such stent delivery balloon catheter designs consist of an elongated catheter tube having two separate distal ends, each of which includes an inflation balloon. Further, based on the respective sizes of the branched vessels of the treatment site, the balloon sizes may vary. In practice, a bifurcated stent is crimped into the dual balloons to obtain a low profile to allow for passage through the patient's vasculature. The dual balloon catheter and crimped stent are advanced over guide wires to the bifurcated vessel treatment site. The balloons are then inflated to expand and secure the Y-shaped stent to the bifurcated vessel. In addition to the problems described above with properly inflating a multiple balloon catheter, bifurcated stent delivery balloon catheters present problems associated with the simultaneous inflation of multiple balloons. For example, the simultaneous inflation of multiple balloons typically involves the use of multiple sources of pressurized inflation fluid requiring the participation of more than one person. This is particularly the case when different sized balloons are used, as the inflation fluid must be injected into the various balloons at different pressure levels.

A third category of balloon catheters is drug delivery catheters. Various drug delivery catheter designs and procedures have been developed for the delivery of therapeutic and/or diagnostic agents to a specific site within a patient's vasculature or bodily organ. Typically, such drug delivery catheter designs include a balloon having a plurality of apertures spaced about its surface located at the distal end of a catheter tube. The interior of the balloon is in fluid communication with an inflation lumen which extends throughout the length of the catheter tube. After the balloon has been positioned within the patient's vasculature or other bodily organ at the treatment site, inflation fluid comprising a therapeutic or diagnostic agent is injected under pressure through the inflation lumen and into the balloon. The balloon expands under the pressure of the inflation fluid and presses against the body wall at the treatment site. The pressurized inflation fluid then migrates through the apertures in the balloon wall and penetrates the tissue wall at the treatment site. The balloon apertures are sized such that the balloon remains pressure-inflated despite the flow of the fluid agent through the apertures of the balloon wall.

Perforated balloon drug delivery catheters such as the one described above are capable of delivering a wide range of therapeutic and/or diagnostic agents. For example, perforated balloon catheters are designed for use in conjunction with angioplasty dilatation for treating the site of an opened atherosclerotic lesion or stenosis with a therapeutic agent such as heparin to inhibit unregulated smooth muscle cell proliferation and prevent restenosis. Alternatively, perforated balloon catheters may be used to deliver a drug or agent to dissolve a stenosis in an effort to avoid use of angioplasty or atherectomy procedures, or to deliver a thrombolytic agent to dissolve a clot at the lesion site. In addition, perforated balloon catheters may also be used to administer antibiotics or anesthetics directly to the treatment site prior to removal of the catheter. Other agents which may be administered through perforated balloon catheters include steroids for suppressing inflammation in a localized tissue site, anti-neoplastic for treating a tumor site, chemotherapeutics or any desired mixture of individual pharmaceuticals.

However, despite the development of this broad range of applications for perforated balloon drug delivery catheters, improvement in the control of the infusion of the inflation fluid to the treatment site is desirable. Typically, the inflation fluid is manually injected into the drug delivery balloon catheter by means of a syringe device comprising a syringe barrel and plunger. Accordingly, the rate of infusion of the inflation fluid and pressurization of the balloon depends on the pressure applied on the syringe plunger by the administering physician. It has been found that the precise control of the pressure and rate at which the inflation fluid is injected into the catheter is important, requiring great skill on the part of the administering physician. For example, the exertion of excessive pressure on the syringe plunger by the physician may result in over-pressurization of the inflation fluid within the balloon, such over-pressurization may cause high velocity jetting of the inflation fluid through the balloon apertures and possible trauma to the interior walls of the patient's vasculature.

Moreover, with regard to each of the above-described balloon catheters, it has been found that the use of a pressure gauge to assist the physician does not assure precise control of the pressure at which the inflation fluid is injected into a balloon catheter. For example, a drop in the pressure indicated on the pressure gauge generally causes the physician to accelerate the movement of the syringe plunger into the syringe barrel, thereby resulting in a pressure spike. Any such pressure spike may result in over-pressurization of the balloon and, consequently, over-inflation of an expansion balloon or possible high velocity jetting of inflation fluid through the apertures of a drug delivery balloon.

Thus, there presently exists a compelling and recognized need for a valve apparatus which provides a safe and reliable means for limiting the pressure of inflation fluid introduced into a balloon catheter.

It is, therefore, a principal object of the present invention to provide an apparatus for limiting the pressure of inflation fluid introduced into one or more balloons associated with at least one catheter device.

It is a further object of the present invention to provide an apparatus which may be selectively adjusted to provide different cut-off pressures for the inflation fluid injected in separate balloons of a balloon catheter.

It is a further object of the present invention to provide an apparatus which enables the use of a single source of pressurized fluid for the controlled inflation of a plurality of balloons associated with one or more balloon catheters.

It is a further object of the present invention to provide an apparatus which enables simultaneous inflation of a plurality of balloons associated with one or more balloon catheters.

It is a further object of the present invention to provide an apparatus for use in a drug delivery balloon catheter to limit the pressure of inflation fluid introduced into a perforated balloon and prevent high velocity jetting of inflation fluid through the apertures of the balloon wall.

It is a further object of the present invention to provide an apparatus for use with a drug delivery balloon catheter which may be selectively adjusted to provide different cut-off pressures to accommodate the specific flow characteristics of a variety of therapeutic and/or diagnostic agents.

Objects and advantages of the invention are set forth in part above and in part below. In addition, these and other objects and advantages of the invention will become apparent herefrom, or may be appreciated by practice with the invention, the same being realized and attained by means of instrumentalities, combinations and methods pointed out in the appended claims. Accordingly, the present invention resides in the novel parts, constructions, arrangements, improvements, methods and steps herein shown and described.

SUMMARY OF THE INVENTION

In accordance with the present invention, an apparatus is provided for limiting the pressure of inflation fluid injected into one or more balloons of a catheter device during a catheterization procedure.

A basic embodiment of the present invention comprises an elongated cylindrical housing having a bore extending longitudinally between the housing front wall and back wall. The bore is dimensioned to form a pressure is chamber coupled in fluid communication with a valve chamber. The valve chamber includes an inlet port and outlet port formed in the side wall of the housing. The valve chamber inlet port is coupled in fluid communication with the output port of an inflation/deflation device. The valve chamber outlet port is coupled in fluid communication with an catheter device inflation lumen having a distal end in fluid communication with the interior of a balloon.

The valve chamber is dimensioned to slidably receive a piston, which has a front surface in fluid communication with the pressure chamber and is longitudinally moveable within the valve chamber between a fully open position and a closed position. The piston includes an internal flow path which is configured to enable the flow of pressurized inflation fluid from the inflation/deflation device, through the piston, and to both the pressure chamber and the balloon when the piston is in an open position. The piston also includes a seal means which functions to cut-off the flow of pressurized inflation fluid from the inflation/deflation device to the pressure chamber and the balloon when the piston is in the closed position. The piston is biased in a normally open position by a spring exerting a predetermined force on the back surface of the piston. The piston is moveable within the valve chamber from the normally open position to the closed position under the counteracting force exerted on the front surface of the piston by the pressure of the inflation fluid residing in the pressure chamber. To this end, as the pressure of the inflation fluid within the pressure chamber and balloon increases, the piston is urged toward the closed position against the predetermined spring force. The spring force is selected such that when the pressure of the inflation fluid within the balloon and pressure chamber reaches a maximum allowable pressure, the piston is urged to the closed position and flow of inflation fluid from the to inflation/deflation device to the balloon is discontinued.

In a preferred embodiment of the present invention, the apparatus may be modified to enable independent control of the pressurization of multiple balloons with a single source of inflation fluid. The preferred embodiment comprises a reservoir chamber having an input port coupled in fluid communication with the inflation/deflation device and a plurality of outlet ports, each of which is coupled in fluid communication with a separate elongated cylindrical housing. Each of the cylindrical housings has the same general construction as the cylindrical housing described above in the basic embodiment of the present invention, with exception that the valve chamber outlet port for each cylindrical housing is coupled in fluid communication with a separate balloon. Further, the biasing forces exerted by the spring within each cylindrical housing may be independently selected to provide different maximum allowable pressure levels for each balloon.

DESCRIPTION OF THE PREFERRED EMBODIMENTS

Referring generally to the embodiments of the invention shown in the accompanying drawings, wherein like reference numbers refer to like parts throughout the various views, the basic principles of the broadest aspects of the invention can be appreciated from FIGS. 1–7.

Figure 1:
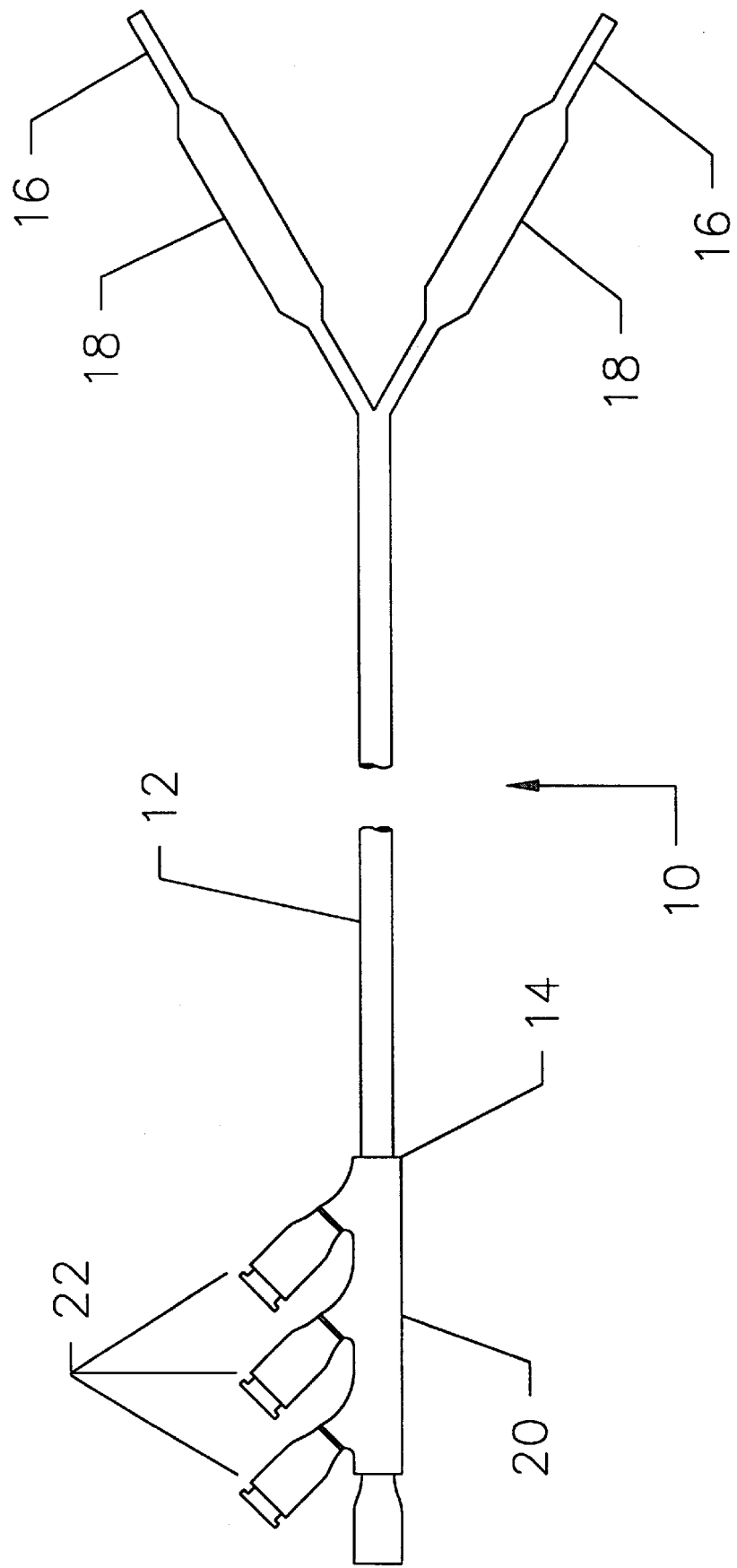
FIG. 1 is a schematic drawing showing a plan view of a bifurcated stent delivery balloon catheter to which the present invention may be applied.

As shown in FIG. 1, a balloon catheter 10 generally comprises a flexible elongate catheter tube 12 having respective proximal and distal ends, 14 and 16. Depending on the particular design and intended use of the catheter device, one or more balloons 18 may be mounted in various arrangements at the distal end 16 of catheter tube 12. For example, the bifurcated stent delivery balloon catheter shown in FIG. 1 includes a separate balloon 18 mounted at each of the bifurcated distal ends of catheter tube 12. Catheter tube 12 includes separate inflation lumens (not shown) extending longitudinally throughout essentially its entire length from proximal end 14 to the interior of each balloon 18, and providing fluid communication therebetween. A manifold 20 is coupled to the proximal end 14 of catheter tube 12. Manifold 20 includes one or more injection ports 22, each of which is coupled in fluid communication with a separate inflation lumen. Injection ports 22 are adapted to be sealingly coupled to an inflation/deflation device, such as a syringe (not shown).

Figure 2:
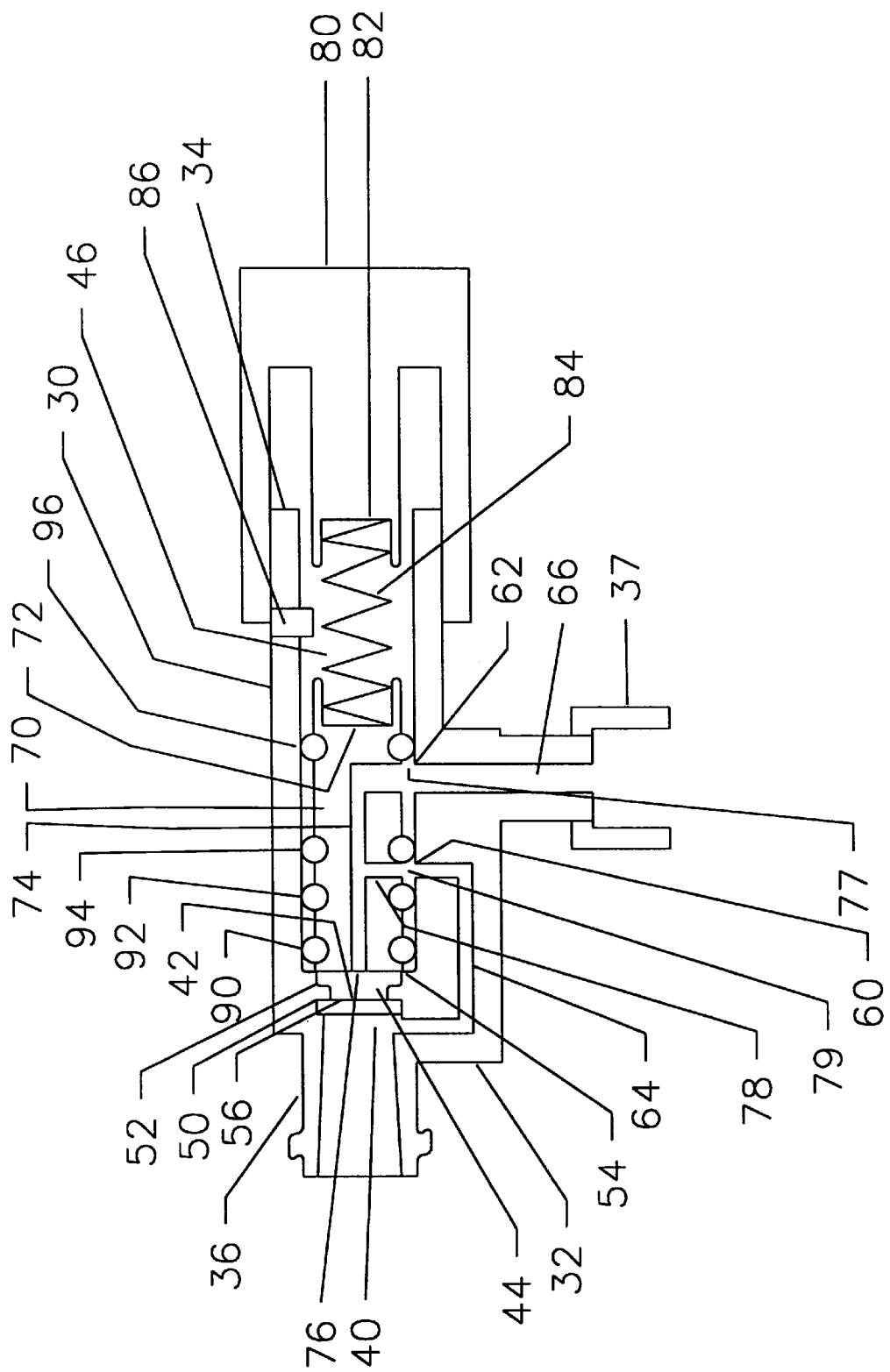
FIG. 2 is a longitudinal cross-sectional view of a single port embodiment of the present invention, wherein the piston is in an open position.

The pressure limiting device of the present invention (as shown in FIG. 2) provides a means for limiting the pressure of inflation fluid injected from an inflation/deflation device to a balloon catheter. To this end, the pressure limiting device of FIG. 2 is preferably coupled in fluid communication between the inflation/deflation device and manifold 20. Alternatively, pressure limiting device 2 may be positioned at any other point in fluid communication between the inflation/deflation device and balloon 18. For example, pressure limiting device 2 may be positioned between manifold 20 and catheter tube proximal end 14.

Referring now to FIG. 2, the present invention is illustrated in a basic form comprising a single port embodiment for limiting the pressure of inflation fluid injected to a single balloon. This embodiment of the present invention comprises an elongated cylindrical housing 30 having a proximal end 32 and a distal end 34. The proximal end of housing 30 includes an input port 36 in the form of a female Luer fitting, which is designed to provide fluid tight engagement with an inflation/deflation device, such as a syringe. Housing 30 further includes a bore extending longitudinally from proximal end 32 to distal end 34, wherein the bore comprises four interconnecting sections. A first section extends from proximal end 32 to annular shoulder 50 and forms an inlet chamber 40. A second section extends from annular shoulder 50 to annular shoulder 52 and defines a passageway 42. A third section extends from annular shoulder 52 to annular shoulder 54 and forms a pressure chamber 44. Finally, a fourth section extends from annular shoulder 54 to open distal end 34 and forms a valve chamber 46.

Inlet chamber 40 includes a one way pressure relief valve 56 to regulate the flow of inflation fluid between pressure chamber 44 and inlet chamber 40. As shown in FIG. 2, pressure relief valve 56 may comprise an elastomeric disk, which is normally seated in fluid tight engagement with annular shoulder 50. In its normal position, seated in fluid tight engagement with annular shoulder 50, valve 56 functions to prohibit the flow of inflation fluid from inlet chamber 40 to passageway 42. However, should the pressure within pressure chamber 44 exceed the pressure within inlet chamber 40, such as when a vacuum pressure is applied to inlet chamber 40, pressure relief valve 56 will become unseated from annular shoulder 50 and permit the flow of inflation fluid from pressure chamber 44, through passageway 42 and into inlet chamber 40.

Valve chamber 46 is preferably cylindrical in shape and is dimensioned to slidably receive a cylindrical piston 70. Valve chamber 46 also includes an inlet port 60 and outlet port 62 formed in its side wall. Valve chamber 46 is coupled in fluid communication with inlet chamber 40 by way of port 60 and conduit 64. Further, valve chamber 46 is provided in fluid communication with output port 37 by way of port 62 and conduit 66. Output port 37 is preferably in the form of a male Luer fitting, which is designed to provide fluid tight engagement with an injection port 22 of manifold 20.

As further shown in FIG. 2, piston 70 includes a bore 74 extending from an outlet 76 formed in the piston front surface to an outlet 77 formed in the piston side wall surface. Bore 74 may take one of many different routes between outlet 76 and outlet 77. For example, as shown in the embodiment illustrated in FIG. 2, bore 74 may extend from outlet 76 longitudinally through the center of piston 70 before turning transversely to outlet 77. Alternatively, bore 74 may extend diagonally through piston 70, thus forming an essentially straight line pathway between outlet 76 and outlet 77. Piston 70 includes a second bore 78, which extends transversely from an inlet 79 formed in the side surface of piston 70 and interconnects with bore 74 at a position between outlet 76 and outlet 77.

Piston 70 is sealingly engaged with the side wall of valve chamber 46 by means of four seal rings, 90, 92, 94 and 96 coupled to the outside side wall surface of piston 70. Referring to FIG. 2, seal ring 90 is disposed adjacent the front end of piston 70. Seal ring 92 is disposed along the length of piston 70 at a position between seal ring 90 and inlet 79. Seal ring 94 is disposed along piston 70 at a position between inlet 79 and outlet 77. Finally, seal ring 96 is disposed immediately adjacent the back end surface of piston 70.

As illustrated in FIG. 2, the distal end 34 of housing 30 is coupled to a removable cap 80 to provide easy access for servicing, replacing and/or repairing the components contained within valve chamber 46. Cap 80, includes a circular seat 82 dimensioned to receive the distal end of a helical compression spring 84. The proximal end of spring 84 is received within a circular seat 72 formed on the back surface of piston 70. According to this arrangement, spring 84 functions to yieldably bias the front surface of piston 70 toward annular shoulder 54. It will be understood that a compression membrane or the like may be used in place of spring 84 to yieldably bias piston 70.

In a preferred form of this single port embodiment, housing 30 and cap 80 are also adjustably coupled such that the longitudinal position of seat 82 within valve chamber 46 may be varied. To this end, the inner side wall of cap 80 is fitted with a screw thread which is designed to mate with a complementary screw thread fitted on the outer side wall of housing 30. It will be understood that by rotating cap 80 relative to housing 30, and thereby varying the longitudinal position of seat 82 within valve chamber 46, the biasing force exerted by spring 84 on piston 70 can be either increased or decreased.

Figure 4:
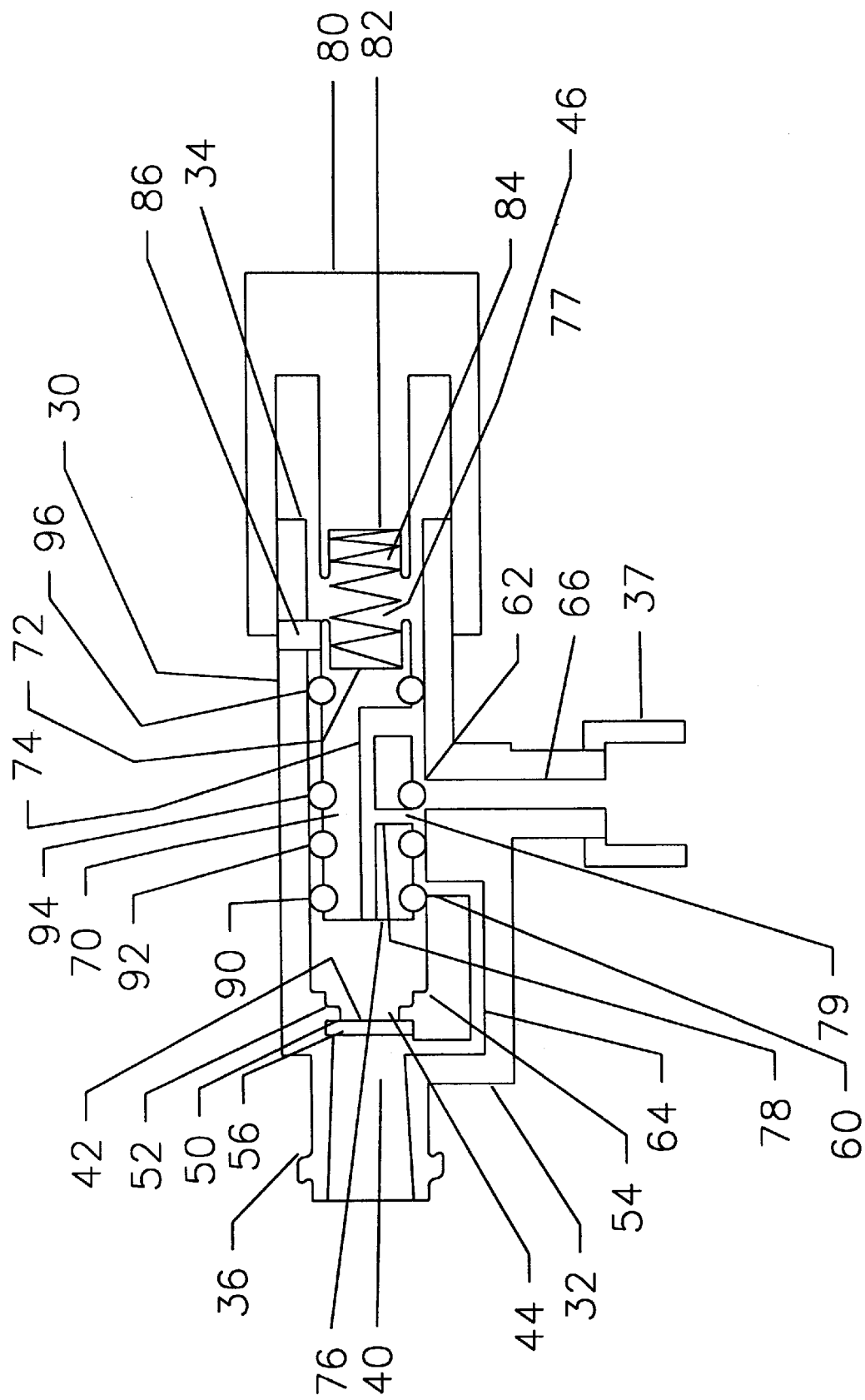
FIG. 4 is a longitudinal cross-sectional view of the embodiment of the present invention shown in FIG. 2, wherein the piston is in a closed position.

Referring now to FIGS. 2 and 4, piston 70 is longitudinally dimensioned in relation to valve chamber 46, such that when piston 70 is in a fully-open position (as shown in FIG. 2), its back end extends to a position whereby seal ring 96 remains engaged with the inner side wall of valve chamber 46 to the distal side of port 62. Further, inlet 79 and outlet 77 of piston 70 are positioned relative to ports 60 and 62 of valve chamber 46 such that, when piston 70 is in the fully open position shown in FIG. 2, inlet 79 is aligned in fluid communication with port 60 and outlet 77 is aligned in fluid communication with port 62. Moreover, as shown in FIG. 4, when piston 70 is in the closed position, inlet 79 is aligned in fluid communication with port 62. In addition, seal rings 90 and 92 are spaced apart along the length of piston 70 such that they form fluid tight seals with the side wall of valve chamber 46 about the proximal and distal sides of port 60, respectively, when the piston is in the closed position shown in FIG. 4. It will be understood that seal rings 90 and 92 can be replaced with a single seal ring which is coupled along its side surface to the side surface of piston 70 such that it encircles and provides a fluid tight seal around port 60 when piston 70 is in the closed position.

Spring 84 is designed to prevent piston 70 from moving within valve chamber 46 past the closed position shown in FIG. 4, such that seal ring 90 remains engaged with the inner side wall surface of valve chamber 46 to the proximal side of port 60. To ensure that piston 70 does not move beyond the closed position, housing 30 may further include a stop pin 86 which extends transversely into valve chamber 46 at a longitudinal position adjacent the distal end of housing 30. To this end, stop pin 86, is designed to provide a physical obstruction which prevents the movement of piston 70 within valve chamber 46 beyond the closed position shown in FIG. 4.

If desired, housing 30 may include a vent port (not shown) for venting air between the portion of the valve chamber 46 distal of piston 70 and the surrounding atmosphere as piston 70 moves between the fully open position shown in FIG. 2 and the closed position shown in FIG. 4.

In operation, the single port pressure limiting device embodiment of the present invention may be coupled in fluid communication between an inflation/deflation device (not shown), such as a syringe, and an indwelling balloon catheter having a balloon positioned across the treatment site of the patient's vasculature. According to this arrangement, a syringe is coupled in fluid communication with the pressure limiting device input port 36, and the pressure limiting device output port 37 is coupled in fluid communication with an injection port 22 of manifold 20. Injection port 22 is further coupled in fluid communication with balloon 18 via an inflation lumen.

Prior to the introduction of pressurized inflation fluid from the inflation/deflation device, the maximum allowable pressure or cut-off pressure for the pressure limiting device is selected by adjusting the longitudinal position of cap 80 relative to housing 30. To aid in the setting of a desired cut-off pressure, the outside surface of housing 30 may be calibrated with a cut-off pressure scale.

Referring now to FIG. 2, piston 70 is initially maintained in the fully open position under the biasing force exerted by spring 84, such that the piston front surface is adjacent annular shoulder 54 and inlet 79 and outlet 77 are aligned in fluid communication with ports 60 and 62, respectively. When the device is in this state, there is provided a continuous flow path for the inflation fluid to pass from input port 36, through inlet chamber 40, conduit 64, interconnecting bores 74, 78 and conduit 66, and out output port 37.

When it is desired to inflate balloon 18, inflation fluid is injected under pressure from a syringe into input port 36. The fluid then travels through inlet chamber 40 and enters conduit 64. The inflation fluid will continue through conduit 64 and into interconnecting bores 78 and 74. The inflation fluid passing through bore 74 will travel bidirectionally toward outlet 76 and outlet 77. Inflation fluid passing through bore 74 and outlet 77 will continue through conduit 66 before exiting output port 37 and entering the balloon catheter. Inflation fluid passing through bore 74 and outlet 76 will enter pressure chamber 44 and passageway 42. To the extent that the pressure of the inflation fluid within inlet chamber 40 is equal to or greater than the pressure of the inflation fluid within passageway 42, one way valve 56 will prevent the passage of fluid from passageway 42 to inlet chamber 40.

It will be understood that since pressure chamber 44 and balloon 18 are coupled in fluid communication, the pressure of the inflation fluid within pressure chamber 44 and balloon 18 will be essentially the same. Further, the pressure of the inflation fluid within pressure chamber 44 exerts a force on the front surface of piston 70 acting opposite the biasing force of spring 84. Thus, as the pressure within balloon 18 and pressure chamber 44 increases, the force exerted on the front surface of piston 70 by the inflation fluid within pressure chamber 44 increases and urges the piston to move longitudinally toward the distal end of valve chamber 46 against the biasing force of spring 84.

Figure 3:
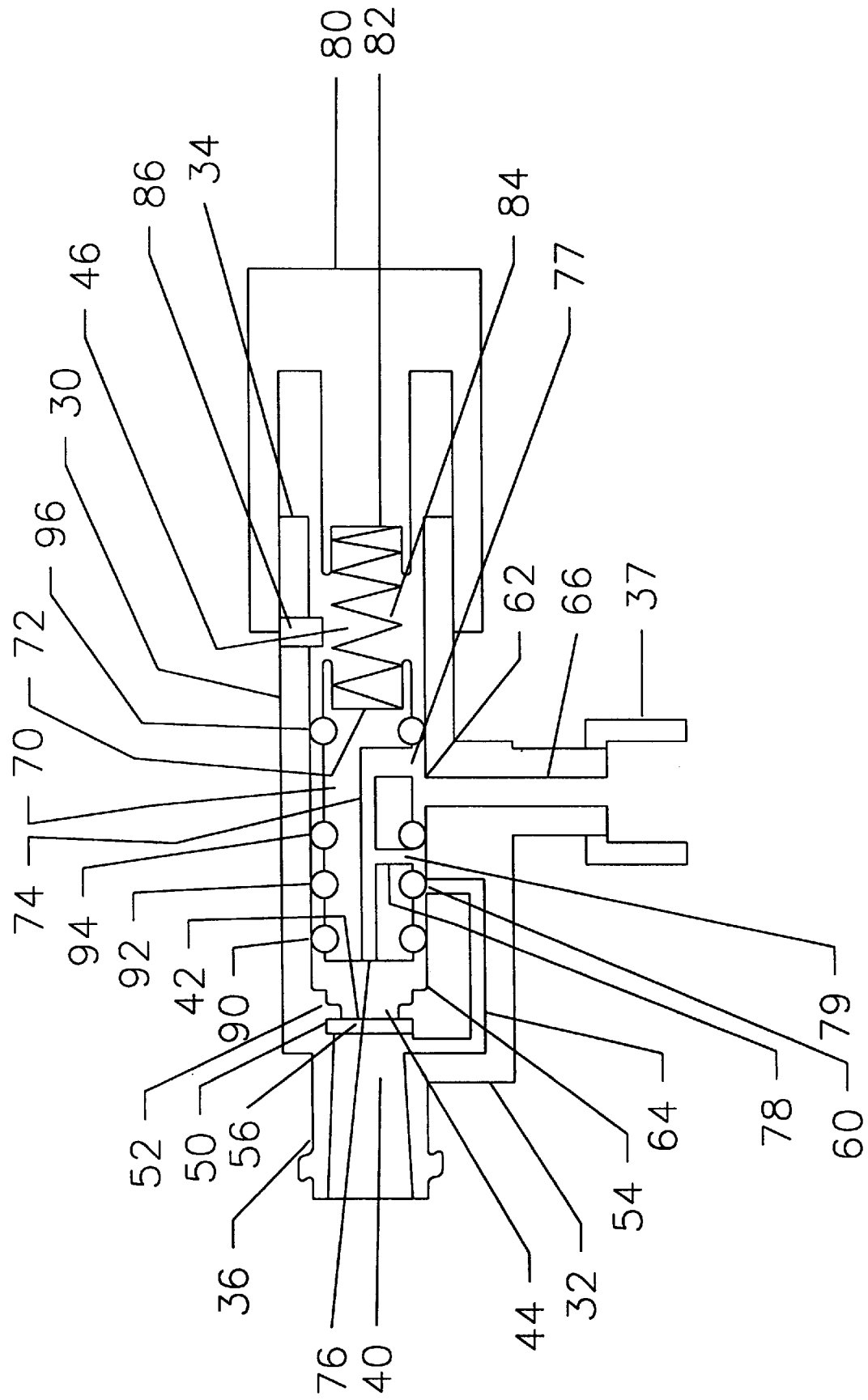
FIG. 3 is a longitudinal cross-sectional view of the embodiment of the present invention shown in FIG. 2, wherein the piston is approaching a closed position.

Referring now to FIG. 3, as the pressure of inflation fluid within balloon 18 and pressure chamber 44 increases and approaches the predetermined cut-off pressure, piston 70 will move longitudinally within valve chamber 46 away from annular shoulder 54 and toward distal end 34. It will be understood that, although piston 70 has moved from the fully-open position shown in FIG. 2 to the intermediate position shown in FIG. 3, the pressure limiting device still provides a continuous flow path between the syringe and balloon catheter.

If, however, the pressure of the inflation fluid within pressure chamber 44 and balloon 18 further increases and reaches the predetermined cut-off pressure, piston 70 will move longitudinally within valve chamber 46 against the biasing force of spring 84 to the closed position shown in FIG. 4. When piston 70 reaches the closed position, seal rings 90 and 92 are positioned about the proximal and distal sides of port 60, thereby cutting off any further flow of pressurized inflation fluid from inlet chamber 40 to balloon 18. As further shown in FIG. 4, pressure chamber 44 remains in fluid communication with balloon 18 when piston 70 is in the closed position via interconnecting bores 74 and 78. Therefore, the pressure of the inflation fluid within pressure chamber 44 and balloon 18 will remain essentially the same.

When the present invention is used with a dilatation balloon catheter or stent delivery balloon catheter, it will be understood that balloon 18 will be fully inflated when piston 70 reaches the closed position. After the balloon is fully inflated for the desired length of time, the administering physician may deflate the balloon by applying a vacuum pressure to inlet chamber 40. Such a vacuum pressure will result in a pressure drop between inlet chamber 40 and pressure chamber 44, whereby pressure relief valve 56 will become unseated from annular shoulder 50 and pressurized inflation fluid will flow from is pressure chamber 44 through passage way 42 to inlet chamber 40. As the inflation fluid flows from pressure chamber 44 to inlet chamber 40, the pressure within pressure chamber 44 decreases. Thus, the force exerted on the front surface of piston 70 by the inflation fluid remaining within pressure chamber 44 also decreases and piston 70 is urged by spring 84 within valve chamber 46 from the closed position shown in FIG. 4 to an open position. Once piston 70 moves from the closed position to an open position, inflation fluid flows from balloon 18 through the flow path provided by conduit 66, interconnecting bores 74, 78 and conduit 64, to inlet chamber 40.

When the single port pressure limiting device is used with a drug delivery catheter having a perforated balloon, piston 70 will similarly be urged toward the closed position as the pressure within balloon 18 and pressure chamber 44 increases and approaches the selected cut-off pressure. Further, should the pressure within balloon 18 and pressure chamber 44 reach the cut-off pressure, piston 70 will move to the closed position, thereby stopping the flow of inflation fluid from inlet chamber 40 to balloon 18. However, unlike with the dilatation balloons as described above, after the pressure within the perforated drug delivery balloon 18 has reached the predetermined maximum allowable pressure and piston 70 has moved to the closed position, the inflation fluid will migrate through the balloon apertures and thereby decrease the pressure of the inflation fluid within balloon 18 and pressure chamber 44. Any such decrease in the pressure of the inflation fluid within pressure chamber 44 will result in the movement of piston 70 from the closed position shown in FIG. 4 to an open position, thereby permitting further flow of inflation fluid from inlet chamber 40 to balloon 18. Should the pressure of the inflation fluid within balloon 18 again reach the cut-off pressure, piston 70 will move to the closed position and stop any further flow of inflation fluid from inlet chamber 40 to balloon 18.

In a preferred form of the present invention, the pressure limiting device comprises a multiple port embodiment adapted to provide independent control over the pressurization of a plurality of balloons with inflation fluid introduced from a common source. For purposes of is illustration, this preferred multiple port embodiment will be described with reference to a dual port pressure limiting device as shown in FIGS. 5–9.

Figure 5:
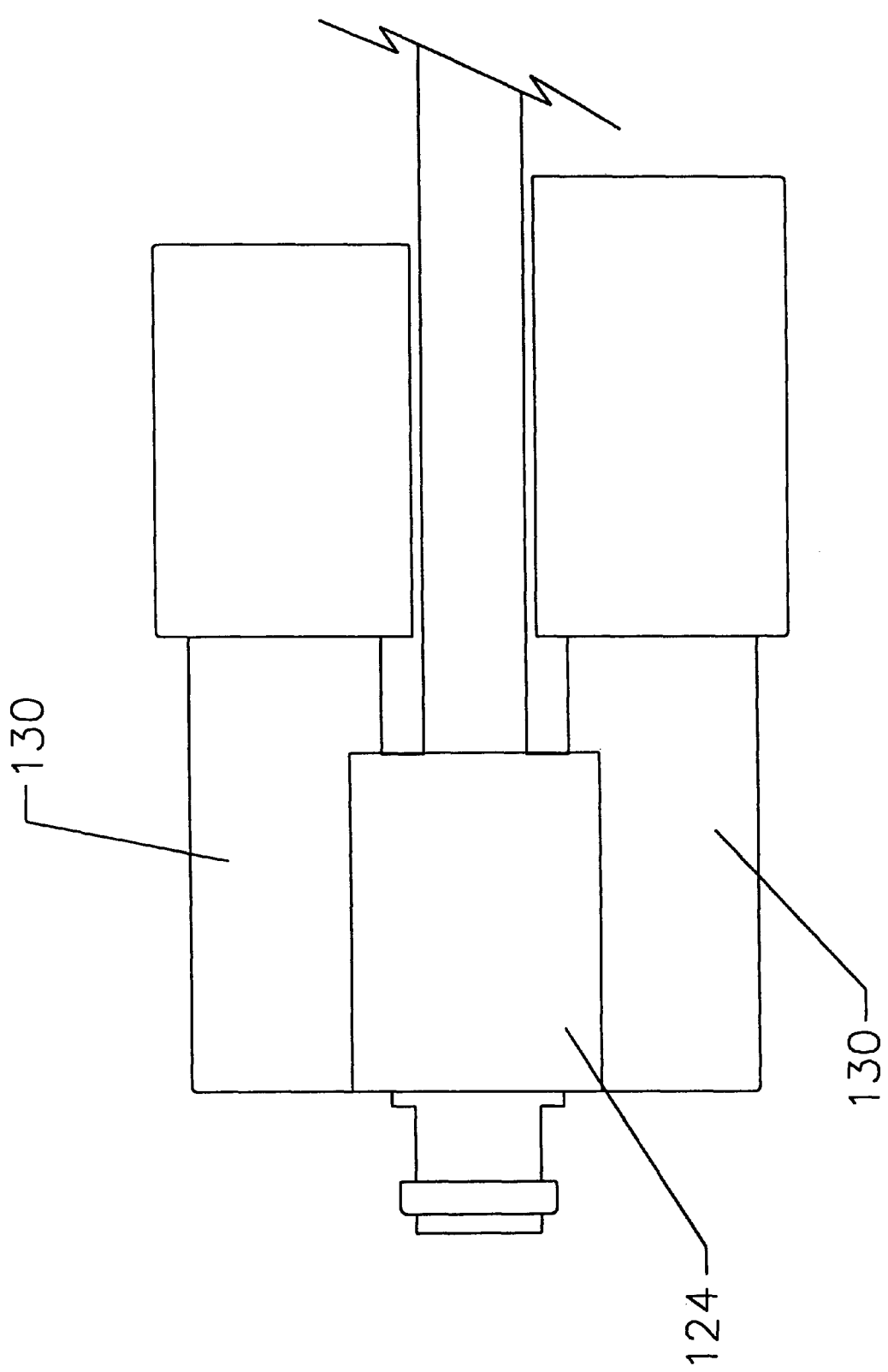
FIG. 5 is a longitudinal plan view of a dual port embodiment of the present invention.
Figure 6:
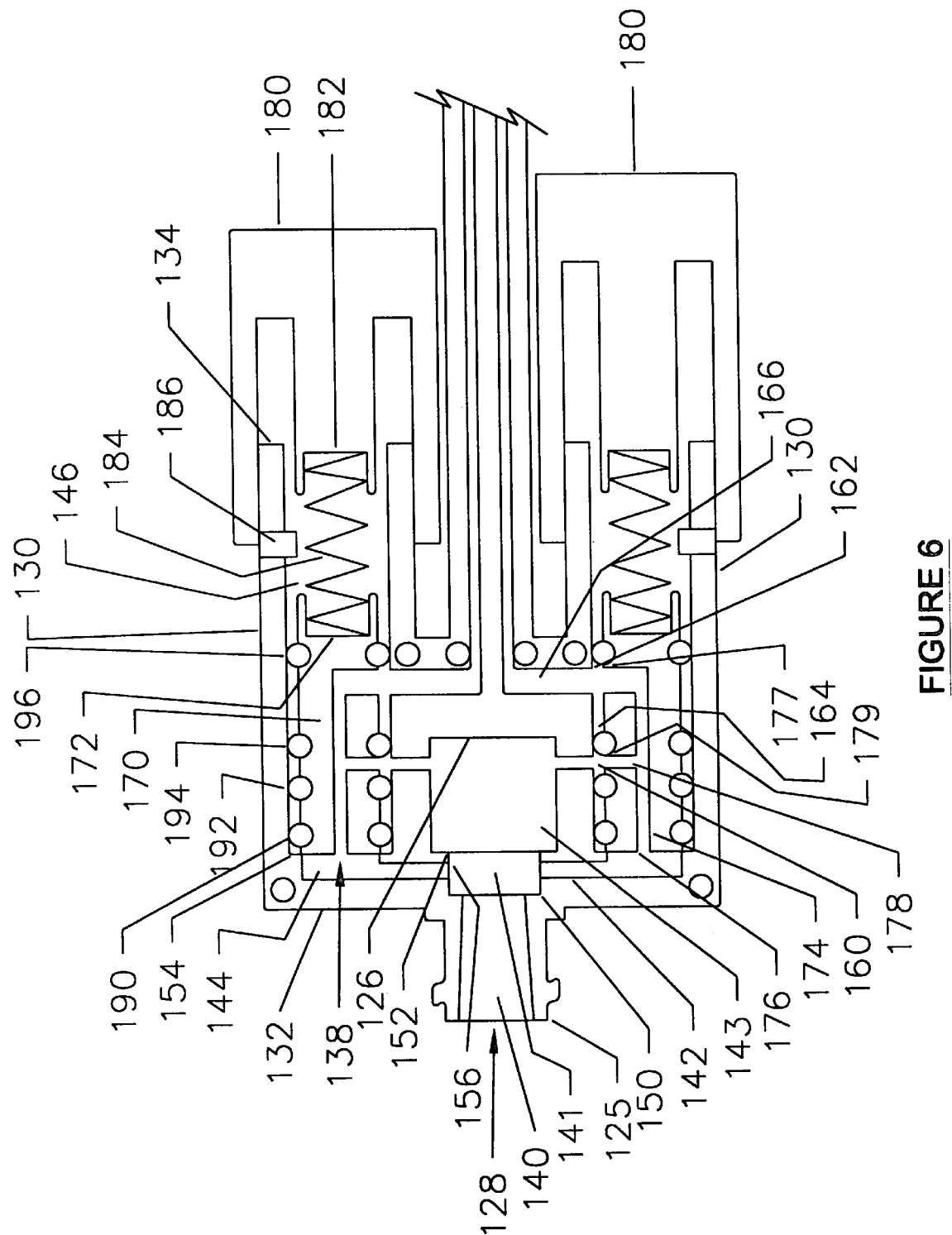
FIG. 6 is a longitudinal cross-sectional view of the embodiment of the present invention shown in FIG. 5, wherein the pistons in both the upper chamber and the lower chamber are in open positions.

Referring to FIG. 5, the preferred dual port embodiment comprises a three-part housing structure having a central body 124 and two valve bodies, each designated as 130. Referring now to FIG. 6, central body 124 preferably comprises an elongated cylinder having a bore 128 extending longitudinally from proximal end 125 to distal wall 126. Proximal end 125 includes an input port 136 in the form of a female Luer fitting, which is designed to provide fluid tight engagement with an inflation/deflation device, such as a syringe.

As shown in FIG. 6, bore 128 comprises three interconnecting sections. A first section comprises an inlet chamber 140, which extends from proximal end 125 to annular shoulder 150. A second section extends from annular shoulder 150 to annular shoulder 152 and forms a transition chamber 141. A third section extends from annular shoulder 152 to distal wall 126 and forms a reservoir chamber 143.

As further shown in FIG. 6, each valve body 130 is disposed about the periphery of central body 124. Preferably, each valve body 130 comprises an elongated cylinder having a proximal wall 132 and a distal end 134. Each valve body 130 further includes a bore 138 extending longitudinally from proximal wall 132 to distal end 134, wherein bore 138 comprises two interconnecting sections. A first section extends from proximal wall 132 to annular shoulder 154 and forms a pressure chamber 144. A second section extends from annular shoulder 154 to distal end 134 and defines a valve chamber 146.

Each valve chamber 146 is preferably cylindrical in shape and is dimensioned to slidably receive a cylindrical piston 170. Each valve chamber 146 also includes an inlet port 160 and an outlet port 162 formed in its side wall. As shown in FIG. 6, each valve chamber 146 is coupled in fluid communication with reservoir chamber 143 through inlet port 160 and conduit 164. Further, each valve chamber 146 is provided in fluid communication with a separate output port (not shown) through outlet port 162 and conduit 166. Each output port is preferably in the form of a male Luer fitting, which is designed for fluid tight engagement with an injection port 22 of manifold 20.

Each pressure chamber 144 is coupled in fluid communication with transition chamber 141 via a conduit 142.

Transition chamber 141 includes a one way pressure relief valve 156 to regulate the flow of inflation fluid from pressure chamber 144 to transition chamber 141. As shown in FIG. 6, pressure relief valve 156 may comprise an elastomeric annular ring, which is normally seated in fluid tight engagement with the side wall of transition chamber 141. In its normal position, seated in fluid tight engagement with the side wall of transition chamber 141, valve 156 functions to prohibit the flow of inflation fluid from transition chamber 141 to conduits 142. However, should the pressure within pressure chamber 144 exceed the pressure within transition chamber 141, such as when a vacuum pressure is applied to transition chamber 141, pressure relief valve 156 will become unseated from the side wall of transition chamber 141 at a position adjacent conduits 142 and permit the flow of inflation fluid from pressure chambers 144, through conduits 142 and into transition chamber 141.

Each piston 170 of the preferred dual port embodiment shown in FIGS. 6–9 includes a pair of interconnecting bores 174 and 178. Bore 174 extends from an outlet 176 formed on the front surface of piston 170 to an outlet 177 formed in the side wall surface of piston 170. Bore 174 may take one of many different routes between outlet 176 and outlet 177. For example, as shown in the embodiment illustrated in FIG. 6, bore 174 may extend from outlet 176 longitudinally through the center of piston 170 before turning transversely to outlet 177. Bore 178 extends transversely from an inlet 179 formed in the side wall surface of piston 170 and interconnects with bore 174 at a position between outlet 176 and outlet 177.

Further, each piston 170 is sealingly engaged with the side wall of each valve chamber 146 by means of four seal rings, 190, 192, 194 and 196 coupled to the outside side wall surface of piston 170. Referring to FIG. 6, seal ring 190 is disposed adjacent the front end of piston 170. Seal ring 192 is disposed along the length of piston 170 at a position between seal ring 190 and inlet 179. Seal ring 194 is disposed along piston 170 at a position between inlet 179 and outlet 177. Finally, seal ring 196 is disposed immediately adjacent the back end surface of piston 170.

As illustrated in FIG. 6, the distal end 134 of each valve body 130 is coupled to a separate removable cap 180 to provide easy access for servicing, replacing and/or repairing the components contained within valve chamber 146. Cap 180, includes a circular seat 182 dimensioned to receive the distal end of a helical compression spring 184. The proximal end of spring 184 is received within a circular seat 172 formed on the back surface of piston 170. According to this arrangement, spring 184 functions to yieldably bias the front surface of piston 170 toward annular shoulder 154. It will be understood that a compression membrane or the like may be used in place of spring 184 to yieldably bias piston 170.

In a preferred form of the dual port embodiment, each valve body 130 is adjustably coupled to a separate cap 180, such that the longitudinal position of seat 182 within valve chamber 146 may be varied. To this end, the inner side wall of cap 180 is fitted with a screw thread which is designed to mate with a complementary screw thread fitted on the outer side wall of valve body 130. It will be understood that by rotating cap 180 relative to valve body 130, and thereby varying the longitudinal position of seat 182 within valve chamber 146, the biasing force exerted by spring 184 on piston 170 can be either increased or decreased.

Figure 9:
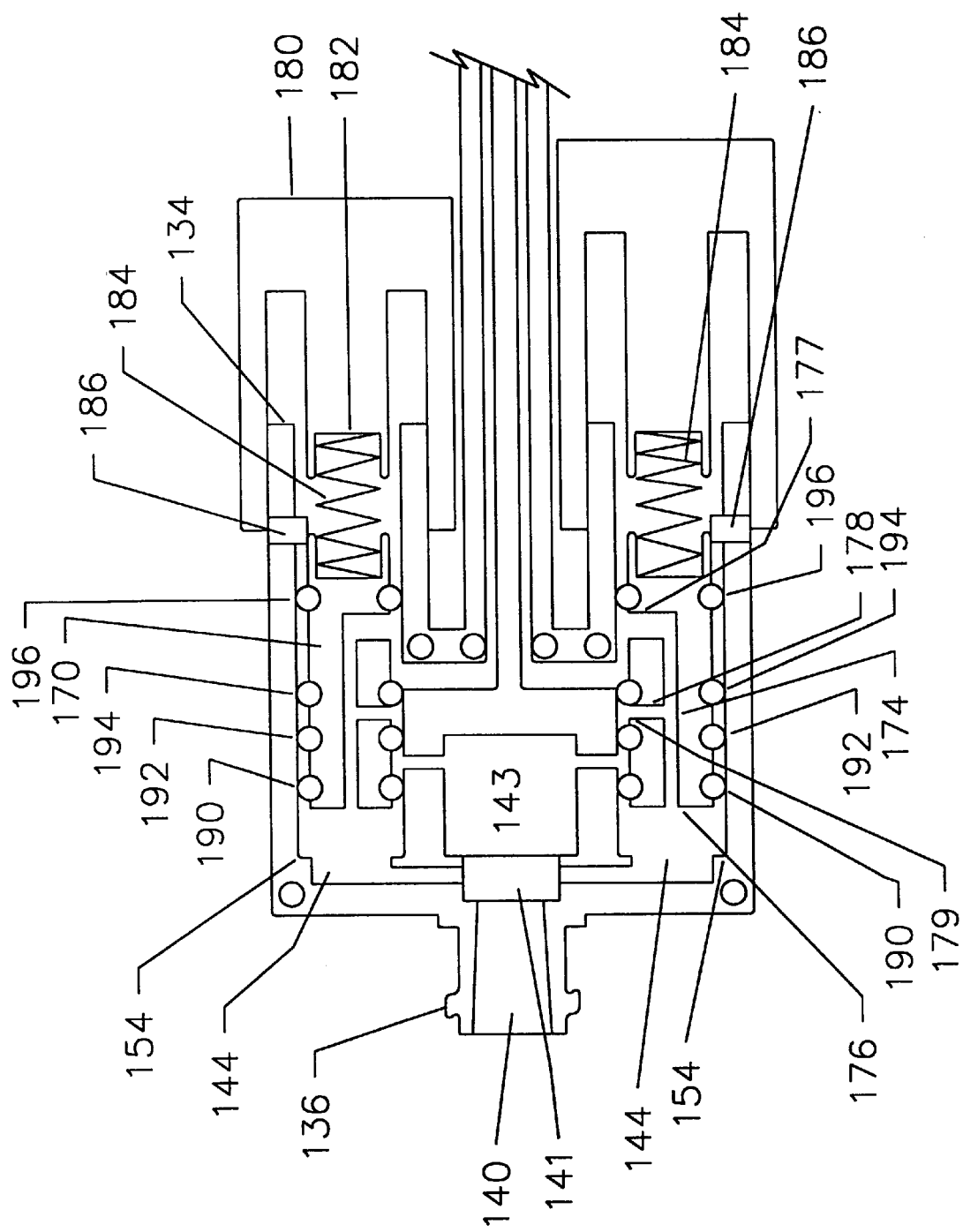
FIG. 9 is a longitudinal cross-sectional view of the embodiment of the present invention shown in FIG. 5, wherein pistons in both the upper chamber and the lower chamber are in closed positions.

Referring now to FIGS. 6 and 9, piston 170 is longitudinally dimensioned in relation to valve chamber 146, such that when piston 170 is in a fully-open position (as shown in FIG. 6), its back end extends to a position whereby seal ring 196 remains engaged with the inner side wall of valve chamber 146 to the distal side of outlet port 162. Further, inlet 179 and outlet 177 of piston 170 are positioned relative to ports 160 and 162 of valve chamber 146 such that, when piston 170 is in the fully-open position shown in FIG. 6, inlet 179 is aligned in fluid communication with port 160 and outlet 177 is aligned in fluid communication with port 162. Moreover, as shown in FIG. 9, when piston 170 is in the closed position, inlet 179 is aligned in fluid communication with port 162. In addition, seal rings 190 and 192 are spaced apart along the length of piston 170 such that they form fluid tight seals with the side wall of valve chamber 146 about the proximal and distal sides of port 160, respectively, when the piston is in the closed position shown in FIG. 9. It will be understood that seal rings 190 and 192 may be replaced with a single seal ring coupled on its side surface at a position on the side surface of piston 170 such that the seal ring encircles and provides a fluid tight seal about port 160 when piston 170 is in the closed position.

Spring 184 is designed to prevent piston 170 from moving within valve chamber 146 past the closed position shown in FIG. 9, such that seal ring 190 remains engaged with the inner side wall surface of valve chamber 146 to the proximal side of port 160. To ensure that piston 170 does not move beyond the closed position, each valve body 130 may further include a stop pin 186 which extends transversely into valve chamber 146 at a longitudinal position adjacent the distal end of valve body 130. To this end, stop pin 186, is designed to provide a physical obstruction which prevents the movement of each piston 170 within its respective valve chamber 146 beyond the fully-closed position shown in FIG. 9.

If desired, each valve body 130 may include a vent port (not shown) for venting air between the portion of the valve chamber 146 distal of piston 170 and the surrounding atmosphere as piston 170 moves between the fully-open position shown in FIG. 6 and the closed position shown in FIG. 9.

For purposes of illustration only, operation of the dual port embodiment will be described with use of the bifurcated stent delivery balloon catheter shown in FIG. 1. It will be understood that the dual port embodiment may be used with any other known type of dual balloon catheter. In addition, the dual port embodiment may also be adapted for use with a single balloon catheter by setting the cut-off pressure of the unconnected valve body to zero.

In operation, the preferred dual port embodiment of the present invention may be coupled in fluid communication between an inflation/deflation device (not shown) and an indwelling bifurcated stent delivery catheter having two balloons 18 positioned at the delivery sites within the patient. According to this arrangement, a syringe or other suitable inflation/deflation device is coupled in fluid communication with the pressure limiting device input port 136. In addition, each output port 137 of the pressure limiting device is coupled in fluid communication with a separate injection port 22 on manifold 20. As described above, each injection port 22 is further coupled in fluid communication with a balloon 18 via a separate inflation lumen.

Prior to the introduction of pressurized inflation fluid from the inflation/deflation device, the maximum cut-off pressure for each of the balloons is fixed by adjusting the longitudinal position of cap 180 for each valve body 130. It will be appreciated that if balloons 18 differ in size, the dual port embodiment of the present invention facilitates independent control of the inflation of the balloons by enabling different cut-off pressures for each balloon. To ensure accurate setting of the cut-off pressures, the outside surface of each valve body 130 may be calibrated with a cut-off pressure scale. For purposes of demonstrating the independent pressure control feature of the preferred dual port embodiment, it will be presumed that, in the working sequence shown in FIGS. 6–9, the cut-off pressure for the top valve body has been set at 12 Bar and the cut-off pressure for the bottom valve body has been set at 8 Bar.

Referring now to FIG. 6, pistons 170 are initially maintained in their fully open positions under the biasing forces exerted by springs 184. When it is desired to simultaneously inflate balloons 18, inflation fluid is injected under pressure from a syringe into input port 136. The pressurized fluid passes through inlet chamber 140 and transition chamber 141 before entering reservoir chamber 143. The pressurized fluid then travels through conduits 164 leading to each valve body 130 and into interconnecting bores 178 and 174 of each piston 170. Once the inflation fluid enters bore 174, a portion will travel through outlet 176 and into pressure chamber 144, whereas the remainder will travel through outlet 177 and conduit 166 and eventually into balloon 18 coupled to the respective valve body 130.

It will be understood that, because pressure chamber 144 and balloon 18 are coupled in fluid communication throughout the inflation procedure, the pressure of the inflation fluid within pressure chamber 144 and balloon 18 will be essentially the same. Further, the pressurized inflation fluid within pressure chamber 144 exerts a force on the front surface of piston 170, which acts opposite the biasing force exerted by spring 184. Thus, as the pressure of the inflation fluid passing from reservoir chamber 143 to each of the valve bodies 130 and balloons 18 increases, each piston 170 will be urged longitudinally within its respective valve chamber 146 in a direction away from annular shoulder 154 and toward distal end 134. The extent to which each piston 170 moves within its valve chamber 146 will depend on the predetermined cut-off pressure selected for each valve body 130. In the present example, since the bottom valve body has been set at a lower cut-off pressure than the top valve body, piston 170 of the bottom valve body will move a greater distance than piston 170 of the top valve body as the pressure of the inflation fluid within reservoir chamber 143, pressure chambers 144, and balloons 18 increases.

Figure 7:
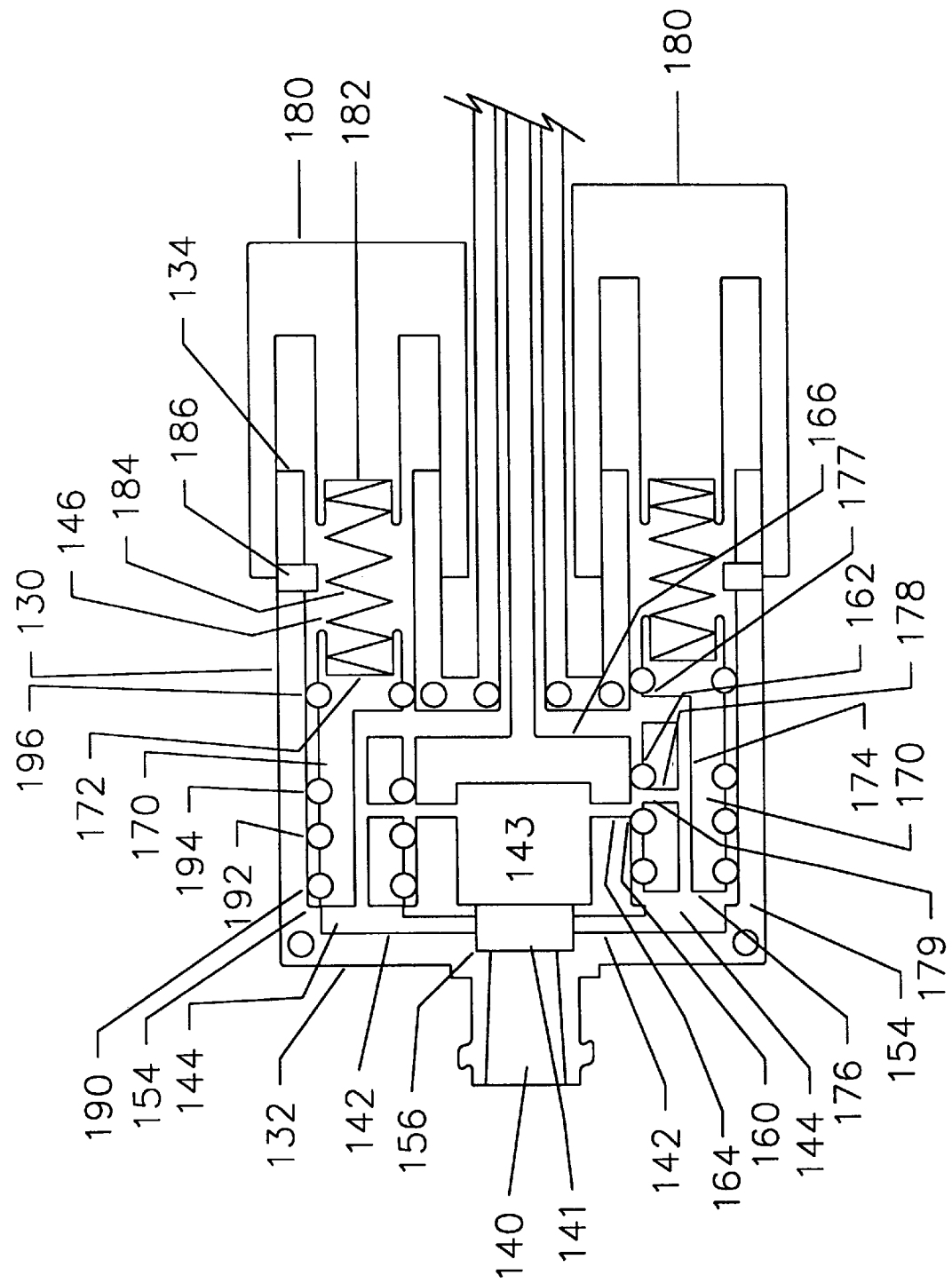
FIG. 7 is a longitudinal cross-sectional view of the embodiment of the present invention shown in FIG. 5, wherein the piston in the lower chamber is approaching a closed position.

Referring now to FIG. 7, as the pressure of the inflation fluid increases and approaches the 8 Bar cut-off pressure selected for the bottom valve body, piston 170 of the bottom valve body will be urged from the fully open position to an intermediate position nearing the closed position. Piston 170 of the top valve body will remain at or near the fully open position. While pistons 170 are in the positions shown in FIG. 7, continuous flow paths remain between the inflation/deflation device and each balloon 18.

Figure 8:
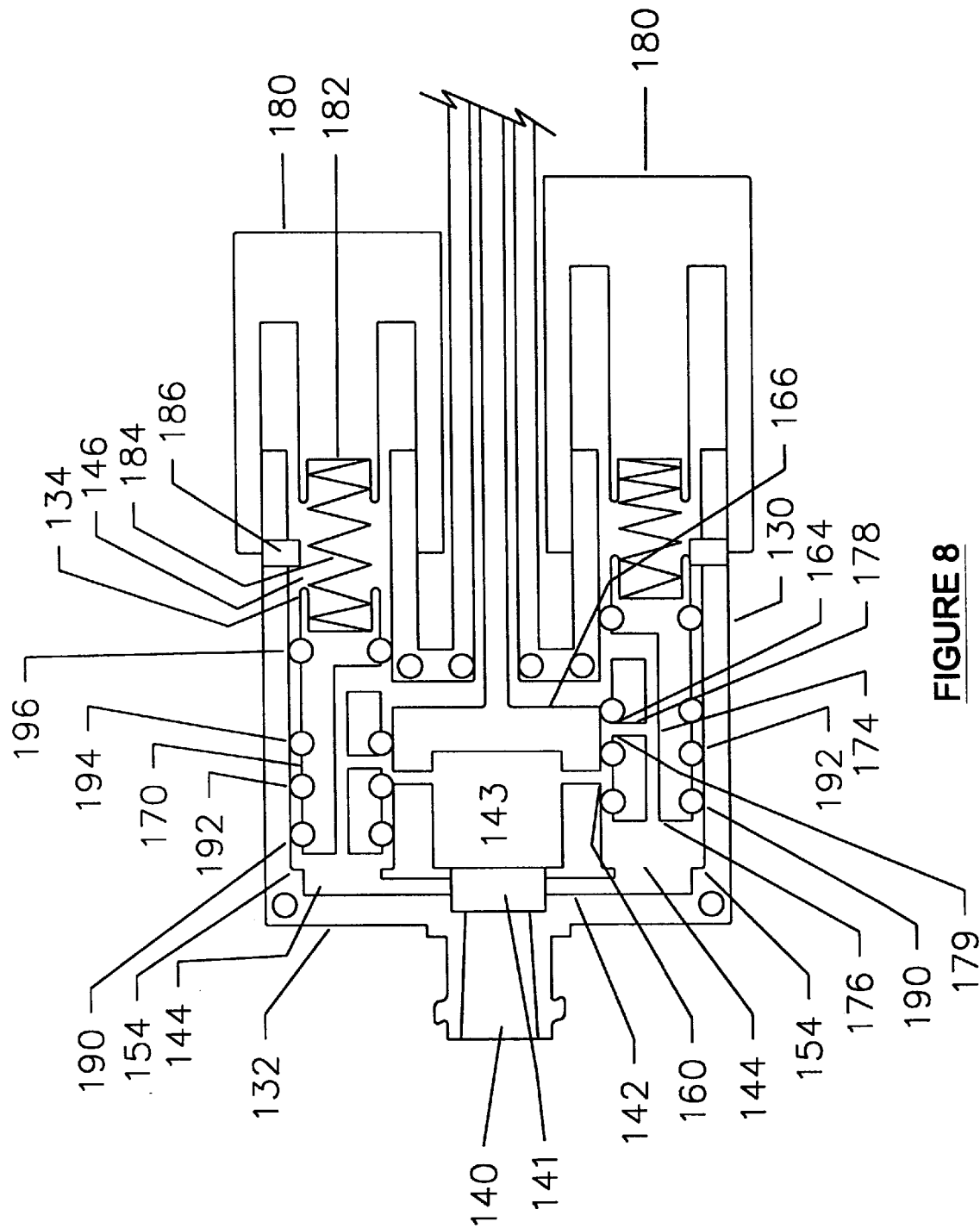
FIG. 8 is a longitudinal cross-sectional view of the embodiment of the present invention shown in FIG. 5, wherein the piston in the lower chamber is in a closed position and the piston in the upper chamber is approaching a closed position.

However, should the pressure of the inflation fluid further increase and reach the 8 Bar cut-off pressure selected for the bottom valve body, piston 170 of the bottom valve body will move to the closed position shown in FIG. 8. In the closed position, piston 170 and seal rings 190 and 192 of the bottom valve body function to cut-off the flow of inflation fluid from reservoir chamber 143 to balloon 18. Since the pressure of the inflation fluid is approaching the 12 Bar cut-off pressure selected for the bottom valve body, piston 170 of the top valve body is urged to an intermediate position. As shown in FIG. 8, a continuous flow path remains between the inflation/deflation device and balloon 18 coupled to the top valve body.

Referring now to FIG. 9, should the pressure of the inflation fluid increase still further and reach the 12 Bar cut-off pressure selected for the top valve body, piston 170 of the top valve body will move to the closed position. In the closed position, piston 170 and seal rings 190 and 192 of the top valve body function to cut-off the flow of inflation fluid from reservoir chamber 143 to balloon 18.

After both balloons 18 have been fully inflated for the desired length of time such that the bifurcated stent is sufficiently secured to the treatment site, the administering physician may deflate the balloons by applying a vacuum pressure to transition chamber 141. Such a vacuum pressure within transition chamber 141 will unseat pressure relief valve 156 from its normal position in fluid tight engagement with the side wall of transition chamber 141. When pressure relief valve 156 is unseated, pressurized fluid within each pressure chamber 144 passes through conduits 142 and into transition chamber 141. As the inflation fluid within pressure chambers 144 flows to transition chamber 141, the pressure within pressure chambers 144 and, consequently, the force exerted on the front surface of each piston 170 decreases. As a result, each piston 170 is urged under the force of biasing springs 184 from the closed position shown in FIG. 9 toward annular shoulder 154. Once pistons 170 move from the closed position, inflation fluid will flow from balloons 18 through the flow path provided by conduit 166, interconnecting bores 174 and 178 and conduits 164 to reservoir chamber 143 and pressure chambers 144.

While only a few embodiments have been illustrated and described in connection with the present invention, various modifications and changes in both the apparatus and method will become apparent to those skilled in the art. For example, while the disclosed embodiments comprise single and dual port pressure limiting devices, the present invention may be modified to simultaneously limit the pressure of inflation fluid injected into three or more inflation ports. All such modifications or changes falling within the scope of the claims are intended to be included therein.

I claim:

1. An apparatus for limiting the pressure of inflation fluid injected from an inflation/deflation device to a balloon catheter, comprising:

a housing having a proximal end, a distal end and a side wall, the housing including;

a valve chamber having a valve chamber inlet port formed in a valve chamber side wall for fluid communication with the inflation/deflation device and a valve chamber outlet port formed in the valve chamber side wall for fluid communication with the balloon catheter;

a pressure chamber coupled in fluid communication with the valve chamber and having a pressure chamber outlet port; and a passageway having an inlet at a distal end thereof and an outlet at a proximal end thereof, wherein the distal inlet is coupled in fluid communication with the pressure chamber outlet port;

a piston disposed within the valve chamber having a proximal surface in fluid communication with the pressure chamber, a distal surface, a side surface, a first piston bore and a second piston bore, wherein the first piston bore forms a first bore passageway extending from a first piston outlet formed in the piston proximal surface to a second piston outlet formed in the piston side surface and the second piston bore forms a second bore passageway extending from a piston inlet formed in the piston side surface to a juncture with the first piston bore, the piston being movable within the valve chamber between an open position wherein the piston inlet is in fluid communication with the valve chamber inlet port and the second piston outlet is in fluid communication with the valve chamber outlet port, and a closed position wherein the piston inlet is in fluid communication with the valve chamber outlet port and the second piston outlet is sealingly closed;

means for yieldably biasing the piston toward an open position within the valve chamber, wherein the means provides a predetermined force, which, when overcome by the force exerted on the piston proximal surface by the pressurized fluid within the pressure chamber, allows movement of the piston within the valve chamber from an open position toward the closed position;

a one-way pressure relief valve operatively associated with the passageway which prohibits the flow of fluid through the passageway to the pressure chamber, and permits, when desired, the flow of pressurized fluid from the pressure chamber through the passageway and out the proximal outlet of the passageway;

a first seal for preventing the flow of inflation fluid to a portion of the valve chamber extending between the piston distal surface and an interior surface of the distal end of the housing; and a second seal for cutting off the flow of inflation fluid from the inflation/deflation device and into the valve chamber when the piston is in the closed position.

2. The apparatus according to claim 1, further comprising a stop means operatively associated with the valve chamber for preventing the piston from moving within the valve chamber beyond the closed position toward the interior surface of the distal end of the housing.

3. The apparatus according to claim 2, wherein the stop means comprises a protrusion extending from a valve chamber side surface.

4. The apparatus according to claim 1, wherein the housing comprises:

a body having a proximal wall, an open distal end, and a side wall, the body including the pressure chamber positioned adjacent the proximal wall of the body and the valve chamber extending to the open distal end of the body;

a cap removably coupled to the open distal end of the body, whereby the cap forms the distal end of the housing.

5. The apparatus according to claim 4, wherein the cap is adjustably coupled to the open distal end of the body such that the valve chamber length and the force exerted on the distal surface of the piston by the biasing means may be varied.

6. The apparatus according to claim 1, wherein the biasing means is one or more springs disposed within the portion of the valve chamber extending between the piston distal surface and the interior surface of the distal end of the housing.

7. The apparatus according to claim 1, wherein the first seal comprises a resilient O-ring mounted to the piston side surface at a position between the piston distal surface and the second piston outlet.

8. The apparatus according to claim 1, wherein the second seal comprises a pair of resilient O-rings mounted along the length of the piston side surface between the piston proximal surface and the piston inlet such that the O-rings form fluid tight seals between the piston side surface and the valve chamber side surface at positions immediately proximal and distal of the valve chamber inlet port when the piston is in the closed position.

9. The apparatus according to claim 1, further comprising:

a reservoir chamber having an input port for fluid communication with the inflation/deflation device, a reservoir chamber outlet port coupled in fluid communication with the valve chamber and a reservoir chamber inlet port in fluid communication with the one-way pressure relief valve;

a first conduit having an inlet end coupled in fluid communication with the reservoir chamber inlet port and an outlet end coupled in fluid communication with the valve chamber inlet port; and a second conduit coupled at an inlet end in fluid communication with the valve chamber outlet port and having an outlet end for fluid communication with the balloon catheter.

10. An apparatus for limiting the pressure of inflation fluid injected from an inflation/deflation device to a plurality of balloons associated with one or more balloon catheters, comprising:

a reservoir chamber having a reservoir chamber input port for fluid communication with the inflation/deflation device and a plurality of reservoir chamber outlet ports;

a plurality of housings, each housing having a proximal end, a distal end and a side wall, wherein each housing includes a valve chamber having a valve chamber inlet port formed in a valve chamber side wall and coupled in fluid communication with one of the reservoir chamber outlet ports and a valve chamber outlet port formed in the valve chamber side wall for fluid communication with a balloon associated with a balloon catheter, and a pressure chamber coupled in fluid communication with the valve chamber and having a pressure chamber outlet port;

a piston disposed within each valve chamber having a proximal surface in fluid communication with the pressure chamber, a distal surface, a side surface, a first piston bore and a second piston bore, wherein the first piston bore forms a first bore passageway extending from a first piston outlet formed in the proximal surface of the piston to a second piston outlet formed in the side surface of the piston and the second piston bore forms a second bore passageway extending from a piston inlet formed in the piston side surface to a juncture with the first piston bore, the piston being movable within the valve chamber between an open position wherein the piston inlet is in fluid communication with the valve chamber inlet port and the second piston outlet is in fluid communication with the valve chamber outlet port, and a closed position wherein the piston inlet is in fluid communication with the valve chamber outlet port and the second piston outlet is sealingly closed;

means associated with each valve chamber for yieldably biasing each piston toward an open position within the valve chamber, wherein the means provides a predetermined force, which, when overcome by the force exerted on the piston proximal surface by the pressurized fluid within the pressure chamber, allows movement of the piston within the valve chamber from an open position toward the closed position;

a passageway operatively associated with each housing, each passageway having an inlet end coupled in fluid communication with the pressure chamber outlet port and an outlet end;

a one-way pressure relief valve operatively associated with the passageway of each housing which prohibits the flow of fluid through the passageway to the pressure chamber, and permits, when desired, the flow of pressurized fluid from the pressure chamber through the passageway and out the outlet end of the passageway;

a first seal operatively associated with each valve chamber for preventing the flow of inflation fluid to a portion of the valve chamber extending between the piston distal surface and an interior surface of the distal end of the housing; and a second seal operatively associated with each valve chamber for cutting off the flow of inflation fluid from the inflation/deflation device and into the valve chamber when the piston is in the closed position.

11. The apparatus according to claim 10, further comprising a stop means operatively associated with each valve chamber for preventing the piston from moving within the valve chamber beyond the closed position toward the interior surface of the distal end of the housing.

12. The apparatus according to claim 11, wherein the stop means comprises a protrusion extending from a valve chamber side surface.

13. The apparatus according to claim 10, wherein each housing comprises:

a body having a proximal wall, an open distal end, and a side wall, the body including the pressure chamber positioned adjacent the proximal wall of the housing body and the valve chamber extending to the open distal end of the body;

a cap removably coupled to the open distal end of the body, whereby the cap forms the distal end of the housing.

14. The apparatus according to claim 13, wherein the cap is adjustably coupled to the open distal end of the body such that the valve chamber length and the force exerted on the distal surface of the piston by the biasing means may be varied.

15. The apparatus according to claim 10, wherein the reservoir chamber further includes a plurality of inlet ports, wherein one of said plurality of reservoir chamber inlet ports is coupled in fluid communication with the outlet end of the passageway associated with each housing.

16. The apparatus according to claim 10, wherein the biasing means for each piston is one or more springs disposed within the portion of the valve chamber extending between the piston distal surface and the interior surface of the distal end of the housing.

17. The apparatus according to claim 10, wherein the first seal associated with each valve chamber comprises a resilient O-ring mounted to the piston side surface at a position between the piston distal surface and the second piston outlet.

18. The apparatus according to claim 10, wherein the second seal associated with each valve chamber comprises a pair of resilient O-rings mounted along the length of the piston side surface between the piston proximal surface and the piston inlet such that the O-rings form fluid tight seals between the piston side surface and the valve chamber side surface at positions immediately proximal and distal of the valve chamber inlet port when the piston is in the closed position.

19. An apparatus for limiting the pressure of inflation fluid injected from an inflation/deflation device to a plurality of balloons associated with one or more balloon catheters, comprising:

a reservoir chamber having an input port adapted for fluid communication with the inflation/deflation device, a plurality of inlet ports and a plurality of outlet ports;

a plurality of housings, each housing comprising (1) a body having a proximal wall, an open distal end, and a side wall, the body including a pressure chamber positioned adjacent the proximal wall of the housing body, a pressure chamber outlet port formed in the pressure chamber coupled in fluid communication with one of said plurality of reservoir chamber inlet ports, a valve chamber extending to the open distal end of the body, and a valve chamber inlet port and a valve chamber outlet port each of said inlet and outlet ports formed in a valve chamber side wall, wherein the valve chamber inlet port is coupled in fluid communication with one of said plurality of reservoir chamber outlet ports and the valve chamber outlet port is for fluid communication with a balloon associated with a balloon catheter, and (2) a cap removably and adjustably coupled to the open distal end of the body, whereby the cap forms a distal wall portion of the housing;

a piston disposed within each valve chamber having a proximal surface in fluid communication with the pressure chamber, a distal surface, a side surface, a first piston bore and a second piston bore, wherein the first piston bore forms a first bore passageway extending from a first piston outlet formed in the proximal surface of the piston to a second piston outlet formed in the side surface of the piston and the second piston bore forms a second bore passageway extending from a piston inlet formed in the piston side surface to a juncture with the first piston bore, the piston being movable within the valve chamber between an open position wherein the piston inlet is in fluid communication with the valve chamber inlet port and the second piston outlet is in fluid communication with the valve chamber outlet port, and a closed position wherein the piston inlet is in fluid communication with the valve chamber outlet port and the second piston outlet is sealingly closed;

one or more springs disposed within each valve chamber for yieldably biasing the piston toward an open position within the valve chamber, wherein each spring provides a predetermined force, which, when overcome by the force exerted on the piston proximal surface by the pressurized fluid within the pressure chamber, allows movement of the piston within the valve chamber from an open position toward the closed position;

a passageway operatively associated with each housing, each passageway having an inlet end coupled in fluid communication with the pressure chamber outlet port and an outlet end coupled in fluid communication with one of said plurality of reservoir chamber inlet ports;

a one-way pressure relief valve operatively associated with the passageway of each housing which prohibits the flow of fluid from the reservoir chamber, through the passageway and into the pressure chamber, and permits, when desired, the flow of pressurized fluid from the pressure chamber through the passageway and into the reservoir chamber;

a resilient O-ring mounted to the side surface of each piston at a position between the piston distal surface and the second piston outlet; and a pair of resilient O-rings mounted along the length of each piston side surface between the piston proximal surface and the piston inlet such that the O-rings form fluid tight seals between the piston side surface and the valve chamber side surface at positions immediately proximal and distal of the valve chamber inlet port when the piston is in the closed position.

20. The apparatus according to claim 19, further comprising a stop means operatively associated with each valve chamber for preventing the piston from moving within the valve chamber beyond the closed position toward the interior surface of the distal end of the housing.

21. The apparatus according to claim 20, wherein the stop means comprises a protrusion extending from a valve chamber side surface.

* * * * *